(12) United States Patent
Foster et al.

(10) Patent No.: US 8,511,551 B1
(45) Date of Patent: Aug. 20, 2013

(54) INFORMATION CARD AND METHOD OF ACCESSING THE SAME

(76) Inventors: Terry B. Foster, St. Paul, MN (US); David N. Kunz, St. Paul, MN (US)

( * ) Notice: Subject to any disclaimer, the term of this patent is extended or adjusted under 35 U.S.C. 154(b) by 458 days.

(21) Appl. No.: 12/315,613

(22) Filed: Dec. 5, 2008

Related U.S. Application Data

(60) Provisional application No. 61/010,747, filed on Jan. 11, 2008.

(51) Int. Cl.
*G06K 5/00* (2006.01)

(52) U.S. Cl.
USPC .......................... 235/382; 235/380

(58) Field of Classification Search
USPC .......................... 235/375, 380, 382
See application file for complete search history.

(56) References Cited

U.S. PATENT DOCUMENTS

| | | | |
|---|---|---|---|
| 3,569,619 A * | 3/1971 | Simjian .................... | 235/380 |
| 4,632,428 A | 12/1986 | Brown | |
| 4,692,603 A | 9/1987 | Brass et al. | |
| 4,728,783 A | 3/1988 | Brass et al. | |
| 4,754,127 A | 6/1988 | Brass et al. | |
| 4,782,221 A | 11/1988 | Brass et al. | |
| 4,939,354 A | 7/1990 | Priddy et al. | |
| 5,027,401 A * | 6/1991 | Soltesz ................... | 380/54 |
| 5,053,609 A | 10/1991 | Priddy et al. | |
| 5,118,369 A | 6/1992 | Shamir | |
| 5,124,536 A | 6/1992 | Priddy et al. | |
| 5,235,172 A | 8/1993 | Oehlmann | |
| 5,243,655 A | 9/1993 | Wang | |
| 5,369,261 A | 11/1994 | Shamir | |
| 5,410,642 A | 4/1995 | Hakamatsuka et al. | |
| 5,420,924 A | 5/1995 | Berson et al. | |
| 5,469,506 A | 11/1995 | Berson et al. | |
| 5,519,200 A | 5/1996 | Williams | |
| 5,522,623 A | 6/1996 | Soules et al. | |
| 5,635,012 A * | 6/1997 | Belluci et al. ............ | 156/277 |
| 5,799,092 A | 8/1998 | Kristol et al. | |
| 5,864,623 A * | 1/1999 | Messina et al. ........... | 340/5.86 |
| 6,005,962 A | 12/1999 | Hirota et al. | |
| 6,189,787 B1 | 2/2001 | Dorf | |
| 6,523,116 B1 | 2/2003 | Berman | |
| 6,695,203 B2 * | 2/2004 | Iki et al. .................. | 235/375 |
| 7,213,759 B2 | 5/2007 | Reichenbach et al. | |
| 2003/0121972 A1 | 7/2003 | Lee et al. | |
| 2004/0199408 A1 | 10/2004 | Johnson | |
| 2004/0232219 A1 | 11/2004 | Fowler | |
| 2005/0067497 A1 | 3/2005 | Jones et al. | |
| 2005/0072846 A1 | 4/2005 | Lubow | |
| 2006/0002591 A1 | 1/2006 | Hombo | |
| 2006/0074713 A1 | 4/2006 | Conry et al. | |
| 2006/0143052 A1 | 6/2006 | Fotsch et al. | |
| 2006/0173718 A1 | 8/2006 | Murphy | |
| 2006/0196929 A1 | 9/2006 | Kelley et al. | |
| 2007/0214005 A1 | 9/2007 | Kennedy | |

\* cited by examiner

*Primary Examiner* — Jamara Franklin

(74) *Attorney, Agent, or Firm* — Richard John Bartz

(57) ABSTRACT

A personal information access card has a PDF417 barcode with an image of the card user encoded therein. The image can be decoded and displayed at the time of presentation of the card to prevent card user misidentification. The barcode has an x-dimension, row height, data columns and a quiet zone which facilitates the use of a scanner to identify and read the barcode to decode the image.

20 Claims, 3 Drawing Sheets

INFORMATION CARD AND METHOD OF ACCESSING THE SAME

CROSS REFERENCE TO RELATED APPLICATION

This application claims the benefit of U.S. Provisional Application Ser. No. 61/010,747 filed Jan. 11, 2008.

FIELD OF THE INVENTION

The invention is directed to an information access card, particularly cards which carry information allowing access to the information carried on the cards and reduce card user misidentification.

BACKGROUND OF THE INVENTION

Recently public hearings have been held on health care reform. One of the proposals under consideration is universal coverage for all health care with mandated insurance coverage, coverage for baskets of care, and medical homes for patients with chronic diseases. The medical home model is designed to link patients with specific family physicians, specialty physicians, hospitals and other health care providers for lifetime care that includes acute, chronic and preventive care. The proposal is for a patient to select a panel of providers that stays with him or her, even though the insurance plan may change from insurance company to insurance company or health plan to health plan, as this provides a better understanding of the patient's physical and mental health conditions. There is a need for a medical card that would hold medical information of a patient which could be used as the patient moves through the health care delivery system.

Card user misidentification is common in electronic transactions and accessing personal information. It is often difficult for businesses and agencies to stop misidentification.

SUMMARY OF THE INVENTION

The information access card of the invention is used to access personalized information, such as a image of a person, encoded in a barcode located on the card.

The card is a generally rectangular semi-flexible plastic card having a front side and a back side. The back side has a magnetic strip and a barcode including an image encoded therein. The barcode has a portable data file 417 barcode format with an x-dimension of at least ten mils. The row height of the barcode is a multiple of the x-dimension. The barcode has at least fifteen columns of data. The quiet zone surrounding the barcode is a multiple of the x-dimension. In one embodiment, the row height and quiet zone are twice the x-dimension.

To capture and encode an image of a person in the barcode, the image is captured using an image capturing device. The captured image is cropped substantially close to the face of the person to edit the captured image for maximum recognition. The captured image is then encoded in the barcode. The encoding process includes the selection of a portable data file 417 barcode format. The error correction level of the barcode is set at a minimum level, such as a zero level. The source from which the image is to be taken is selected. The image source is either a fixed image from a file, a variable image from a file, a variable image from a database. The image source can also be an image that is captured at the time the card is printed. The x-dimension of the barcode is set at ten mils or larger. The row height of the barcode is set as a multiple of the x-dimension, preferably twice the x-dimension. The number of columns of data in the barcode is designated to be at least fifteen columns. The space around the outside of the barcode is left blank. The blank space is set at a multiple of the x-dimension, preferably twice the x-dimension. The barcode is then printed at a selected position of the card. The captured image encoded in the barcode is adapted to be decoded using a scanning device and displayed.

DESCRIPTION OF PREFERRED EMBODIMENT

Figure 1:
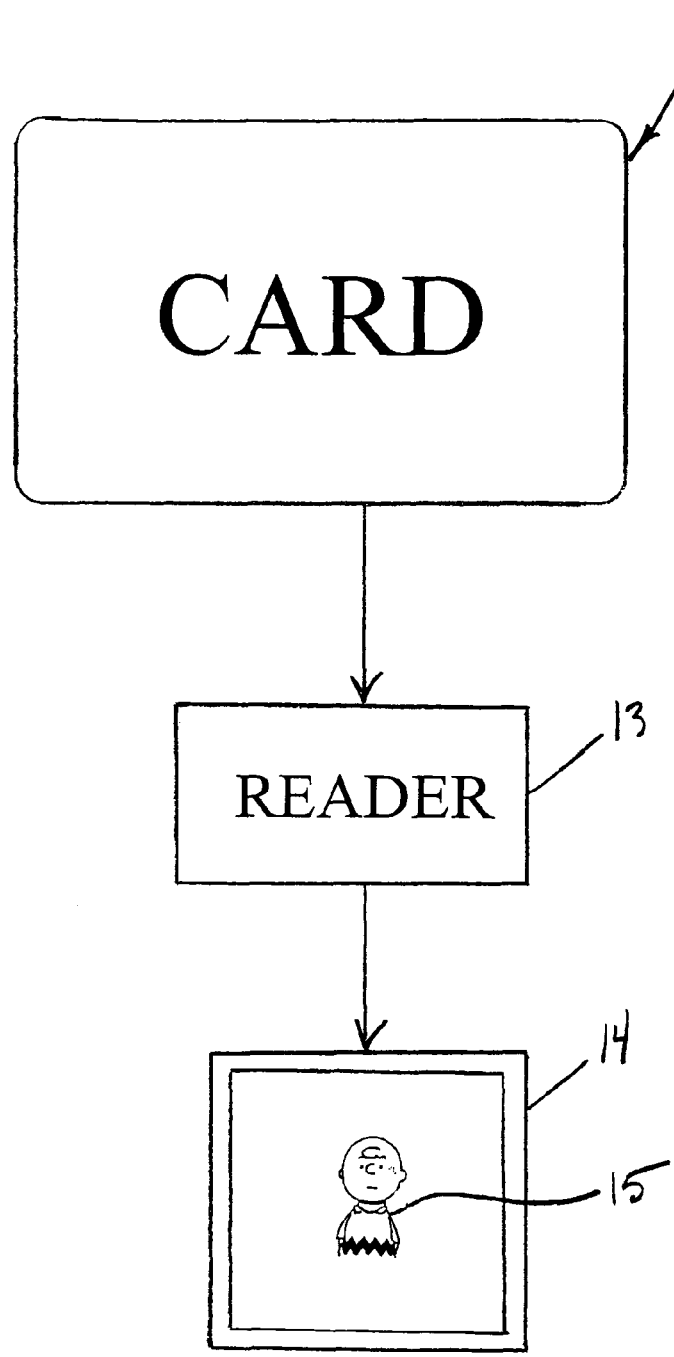
FIG. 1 is a diagrammatic view of the access card of the invention useable with a reader to produce an image of a person.
Figure 2:
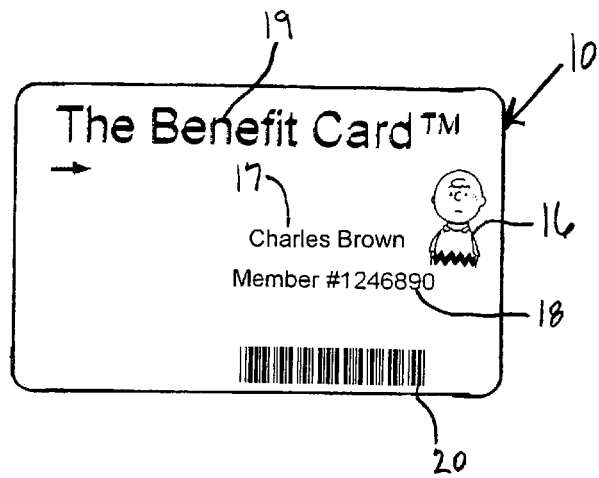
FIG. 2 is a front elevational view of the access card of FIG. 1.
Figure 3:
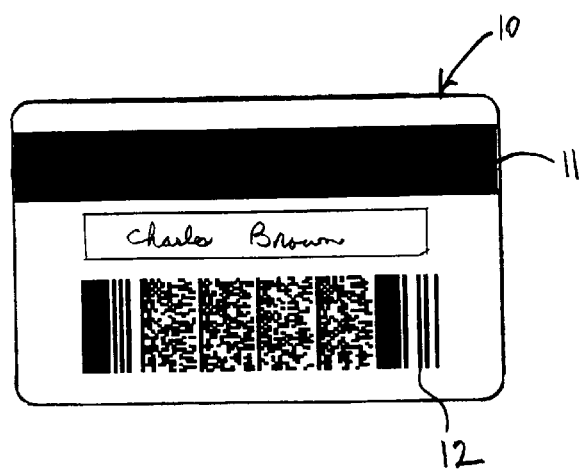
FIG. 3 is a rear elevational view of the access card of FIG. 1.

Referring to FIGS. 1 to 3, there is shown an access card, indicated generally at 10, useable to access various personal information, such as medical, insurance, business, travel, banking, credit and financial information, in a secured manner, and prevent card user misidentification. A scanning device or reader 13 is used to read a magnetic strip 11 and a barcode 12 located on the back of card 10 to gain access to personal information, such as health profiles, financial details, an image 15 of a person and other types of personal information, embedded in strip 11 and encoded in barcode 12. Image 15 can then be immediately displayed on reader 13 or a display device, such as a video monitor display, operatively connected to reader 13. Using banking software and magnetic strip 11, card 10 is capable of functioning as a banking debit and credit card. Image 15 can also be printed on a document 14 from reader 13 or other printing devices. Other positions on card 10 to place magnetic strip 11 and barcode 12 can be determined and selected. The front of card 10 carries a photograph 16 of a person or photographic likeness of one who is the card owner. The front of card 10 also carries conventional human-readable indicia, such as the card holder's name 17, a member number 18, card logo 19, and linear barcode 20. Photograph 16 can be thermally bond or adhesively secured to the face of card 10. Photograph 16 can also be imprinted on the front of card 10.

Barcode 12 is a two-dimensional stacked barcode symbology having a large information capacity. Preferably, barcode 12 has a portable data file 417 format or PDF417 format. Barcode 12 is suitable for use in a wide variety of applications where large amounts of data need to be reliably encoded and decoded including logistics and transportation, retailing, healthcare, government, identification and manufacturing. Barcode 12 has enough capacity to contain an entire data file of information, such as a data file of an image 15 of a person. Barcode 12 can also be used for hazardous materials labeling, storing technical specifications and calibration data on electronic instruments, encoding fingerprints and other biometric information. Plural sets of barcodes may be used for larger data files and multiple information files.

The width or x-dimension of a single bar in barcode 12 has a pre-determined value whereby image 15 encoded in barcode 12 can subsequently be decoded and read by reader 13.

Preferably, the x-dimension of a single bar of barcode 12 is ten mils or 0.01 inches whereby image 15 encoded in barcode 12 can be read by reader 13.

The height of each row of bars in barcode 12 is a multiple of the x-dimension of a single bar of barcode 12. Preferably, the row height is twice or two times the x-dimension or width of the single bar to allow reader 13 to decode image 15 from barcode 12.

Card 10 has a quiet zone or blank space surrounding the outside of barcode 12 to facilitate the use of reader 13 to identify barcode 12. The quiet zone is a multiple of the x-dimension or width of a single bar of barcode 12. Preferably, the quiet zone is twice or two times the x-dimension of a single bar of barcode 12.

Barcode 12 has a level of error correction that allows damaged symbols in barcode 12 to be decoded successfully. Increasing the error correction level allows symbols in barcode 12 to be read even when damaged due to scratching or printing errors. The higher the error correction level, the greater the error correction which results in a decreased amount of photo data that can be stored in barcode 12. Accordingly, the error correction level is preferably set at zero or a lowest level to maximize the amount of photo data that can be stored in barcode 12.

Other types of barcodes can be used as barcode 12. For example, barcode 12 can be a linear barcode capable of accessing an external database, such as an individual's personal medical database and other personal databases. Card 10 can have a plurality of barcodes and magnetic strips containing various information and/or keys.

Image 15 is captured and encoded in barcode 12 using label design software. Barcode 12 containing image 15 is then added to card 10 using a printing program. Card 10 is an existing card design or a card design newly created or a sample card design. Image 15 can be either a black-and-white image of a person or a color image of the person.

Image 15 encoded in barcode 12 is configured from an existing image file or a captured photo for one time use. Image 15 can also be a variable image configured from a file stored on an outside database or the Internet. The name of the image file is built using data from the current database record. For example, each image file can be named using a combination of the person's first and last names. Other names for the image file can be use to identify the file. Image 15 can also be a variable image stored in a database field containing the image data. Image 15 can be captured at the time the card is printed and not stored in a database or as a file, if desired.

Reader 13 has decoding or reading software to read barcode 12 to access the personal information and data file of image 15 encoded in barcode 12 and display the personal information and image 15 on reader 13 or display device operatively connected to reader 13 or transmit the personal information and/or image 15 to an off-site location. The decoding software utilized to decode barcode 12 allows production and interpretation of secure code data stored in barcode 12. Also, image 15 can be printed on document 14. Displaying image 15 and transmitting image 15 prevents the use of card 10 by someone who does not bear a semblance to image 15. When card 10 is presented to reader 13 and the operator of reader 13 compares image 15 which reader 13 reads and displays against the appearance of the card holder, any mismatch is discovered. Verification may be accomplished at a point of use using a point of use device or forwarded to a centralized database in a networked off-site system.

Misidentification of a card holder or user is prevented with use of card 10. The data file containing image 15 encoded in barcode 12 is accessible by scanning barcode 12 with reader 13. Image 15 can be either a black-and-white image or a color image. Image 15 is displayed on reader 13 at the point of time of presentation for comparison with the appearance of the user. Image 15 can also be transmitted to different locations for review and comparison with images stored on outside databases and/or printed on a document 14 to minimize misidentification of the card holder.

Figure 4:
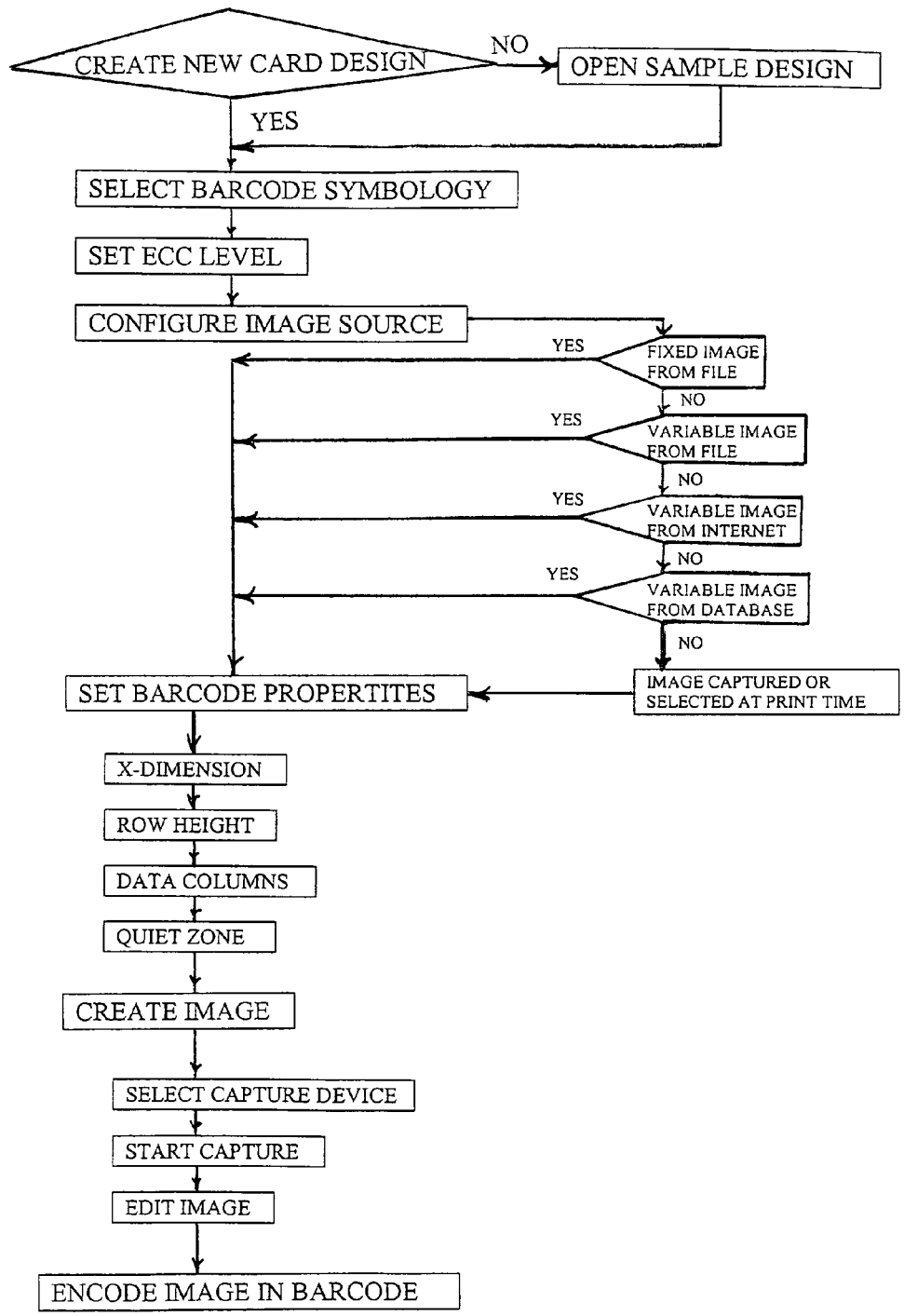
FIG. 4 is a flow chart explaining the method of capturing and encoding an image in a barcode in accordance with the invention.

In use, a barcode 12, such as a PDF417 barcode, containing an image 15 is added to card 10. Image 15 is first captured and encoded in barcode 12. To encode image 15 in barcode 12, as seen in FIG. 4, a new card design is created or a sample card design is selected. A position on the card design to place barcode 12 is determined and selected. The type of barcode symbology is selected and the error correction level is set. Preferably, the barcode symbology is a PDF417 barcode format and the error correction level is set at zero. Image 15 to be encoded in barcode 12 is then configured. Image 15 can be configured from an existing image file or a captured photo for one time use. Image 15 can also be a variable image configured from a file stored on an outside database or the Internet. The name of the image file is built using data from the current database record. Each image file is named using a combination of the person's first and last names. Other names or designations for the image file can be used to identify the file. Image 15 can also be configured from a photo stored in a database field containing the photo data. The database field containing the image data can be selected for an image that is stored in a database field. Image 15 can also be configured from an image captured or selected at print time and not stored in a database or as a file. A title of image 15 is specified. Also, how often the user is prompted for a new image while printing cards is specified. For example, it can be specified to seek a new image for every card printed or after a selected number of cards printed. The characteristics of barcode 12 are then set. The width or x-dimension of a single bar in barcode 12 is set in mils or thousands of an inch. Increasing the x-dimension of the single bars of barcode 12 increases the overall size of barcode 12. The x-dimension is selected so that when image 15 is encoded on barcode 12 it can subsequently be read by reader 13. Preferably, the x-dimension of a single bar of barcode 12 is ten mils or 0.01 inches to ensure image 15 encoded on barcode 12 can be read by reader 13. The x-dimension can be larger than ten mils. The height of each row of bars is set as a multiple of the x-dimension of a single bar of barcode 12. Preferably, the row height is twice or two times the x-dimension or width of the single bar when image 15 is encoded in barcode 12. The number of columns of data in barcode 12 is set. Increasing the number of columns increases the width of barcode and decreases the height of barcode 12. Preferably, the number of data columns is fifteen. The quiet zone or blank space surrounding the outside of barcode 12 facilitating the use of reader 13 to identify barcode 12 is set as a multiple of the x-dimension or width of a single bar of barcode 12. Preferably, the quiet zone is twice or two times the x-dimension of the bar of barcode 12. Barcode 12 can be sent separately from other card design data to allowing a printer to easily print barcode 12 using a K-black resin panel whereby barcode 12 is easier to scan. The position and orientation of barcode 12 on card 10 is then determined and selected. Card 10 can be a landscape card of a portrait card. Barcode 12 can be printed using a thermal transfer printer.

Image 15 can be captured with a capture device, such as a camera interfaced to a computer. Launching the camera software allows the positioning of the camera whereby a picture may be taken. After image 15 has been captured, image 15 is then cropped as closely around the individual's face as possible to maximize recognition when viewing the scanned barcode.

The present disclosure are preferred embodiments of the access card and methods of making and using the same. The present invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

The invention claimed is:

1. A method of identifying a user of a card and accessing personal information of the user, the card having at least one barcode, comprising:
   storing an encoded facial image of a user of a card in a barcode located on the card;
   fixing a photographic likeness of the user to the card;
   storing personal information associated with the user of the card in the barcode, the personal information including unique control data representing medical and financial information that the user makes available;
   scanning the barcode to access the image and medical and financial information stored in the barcode;
   displaying the image on a video display;
   comparing the image displayed on the video display and the photographic likeness to the appearance of the user at the time of presentation of the card to authenticate the identity of said user;
   accessing the medical and financial information after authenticating the identity of the user; and
   using said unique control data to access, identify and select a portion of the medical and financial information to execute desired medical or financial services for the user.

2. The method of claim 1 including:
   accessing an external personal database of the user after authenticating the identity of the user.

3. The method of claim 1 including:
   scanning the barcode with a reader to read the image; and
   printing the image from the reader to authenticate the identity of the user.

4. The method of claim 1 wherein:
   the image is a black-and-white or color image adapted to be displayed on the video display to authenticate the identity of the user.

5. A personalized card comprising:
   a generally rectangular semi-flexible plastic card having a front side and a back side opposite from the front side;
   a photographic likeness of a person and human-readable indicia located on the front side of the card;
   a magnetic strip containing personalized information located on the back side of the card;
   a barcode located on the back side of the card adjacent the magnetic strip;
   an image of the person encoded in the barcode; and
   personal information for the person encoded in the barcode, the personal information including unique control data representing medical and financial information that the person makes available;
   whereby the barcode is adapted to be read with a scanning device to decode and display the image on a video display and compare the image displayed on the video display and the photographic likeness to the appearance of the person at the time of presentation of the card to authenticate the identity of said person and access, identify and select a portion of the medical and financial information using the unique control data to execute desired medical or financial services to the person.

6. The card of claim 5 wherein:
   the image is a black-and-white or color image adapted to be read by the scanning device to authenticate the image of the person, the medical and financial information being accessed after authenticating the image of the person.

7. A method of capturing, encoding and accessing an image and personal information of a person in a barcode comprising:
   capturing an image of a person using an image capturing device;
   cropping the captured image substantially close to the face of the person to edit the captured image for maximum recognition;
   encoding the captured image in a barcode, the encoding including
   selecting a barcode format;
   setting an error correction level of the barcode at a minimum level;
   selecting an image source;
   setting an x-dimension of the barcode to at least 10 mils or larger;
   setting a row height of the barcode as a multiple of the x-dimension;
   selecting a number of columns of data in the barcode at fifteen or more;
   setting a blank space surrounding the outside of the barcode as a multiple of the x-dimension;
   storing personal information of the person in the barcode, the personal information including unique control data representing medical and financial information that the person makes available;
   printing the barcode at a selected position on a card;
   decoding the barcode to access the captured image and personal information;
   displaying the image on a display device to authenticate the image of the person;
   comparing the displayed image to the appearance of the person at the time of presentation of the card to authenticate the identity of said person;
   accessing the medical and financial information using the unique control data, the medical and financial information being accessed after authenticating the image of the person; and
   using said unique control data to identify and select a portion of the medical and financial information to executed desired medical or financial services for the person.

8. The method of claim 7 wherein:
   the image displayed is a black-and-white image or color image.

9. The method of claim 7 wherein:
   the captured image is displayed using a printing device operatively connected to the scanning device to print the image.

10. The method of claim 7 wherein:
    the captured image is displayed on a video monitor display device operatively connected to the scanning device to display the image.

11. The method of claim 7 wherein:
    the image source is a fixed image from a file.

12. The method of claim 7 wherein:
    the image source is a variable image from a file.

13. The method of claim 7 wherein:
the image source is a variable image from the Internet.
14. The method of claim 7 wherein:
the image source is a variable image from a database.
15. The method of claim 7 wherein:
the image source is an image captured at the time the card is printed.
16. The method of claim 7 wherein:
the barcode format is a portable data file 417 format.
17. The method of claim 7 wherein:
the barcode is printed on the card using a k-black resin panel.
18. The method of claim 7 wherein:
the error correction level of the barcode is set at a zero level.
19. The method of claim 7 wherein:
the row height of the barcode is set at twice the x-dimension.
20. The method of claim 7 wherein:
the blank space surrounding the barcode is set at twice the x-dimension.

\* \* \* \* \*